(12) United States Patent
Paul et al.

(10) Patent No.: US 7,049,467 B2
(45) Date of Patent: May 23, 2006

(54) PROCESS FOR THE MANUFACTURE OF ISOBUTYRIC ANHYDRIDE

(75) Inventors: Jean-Michel Paul, Metz (FR); Patrick Busca, Bening les Saint-Avold (FR)

(73) Assignee: Arkema, Puteaux (FR)

( * ) Notice: Subject to any disclaimer, the term of this patent is extended or adjusted under 35 U.S.C. 154(b) by 0 days.

(21) Appl. No.: 10/824,618

(22) Filed: Apr. 15, 2004

(65) Prior Publication Data

US 2005/0014974 A1 Jan. 20, 2005

(30) Foreign Application Priority Data

Apr. 16, 2003 (FR) .................................. 03 04785

(51) Int. Cl.
*C07C 51/56* (2006.01)

(52) U.S. Cl. ...................................... 562/895; 562/888

(58) Field of Classification Search ................ 562/887, 562/888, 893, 895, 896, 898
See application file for complete search history.

(56) References Cited

U.S. PATENT DOCUMENTS 4,857,239 A * 8/1989 Hurtel et al. ............... 562/896

FOREIGN PATENT DOCUMENTS

| EP | 0 004 641 | 10/1979 |
| EP | 0004641 | * 10/1979 |
| FR | 784 458 | 7/1935 |
| FR | 2 514 345 | 4/1983 |

* cited by examiner

*Primary Examiner*—Johann Richter
*Assistant Examiner*—Karl Puttlitz
(74) *Attorney, Agent, or Firm*—Millen White Zelano Branigan P.C.

(57) ABSTRACT

This process for the manufacture of isobutyric anhydride by reacting acetic anhydride with isobutyric acid, distilling the acetic acid generated as it is formed, is characterized in that the reactor is initially loaded with at least a portion of one of the reagents and a portion of the other such that the reagents are in an excess molar ratio relative to the stoichiometry of one of the reagents, and the reaction is carried out while adding the remainder of the reagents as the reaction progresses and according to the place left free in the reactor by the distillation of the acetic acid produced by the reaction, until the desired overall molar ratio of the reagents is reached.

11 Claims, No Drawings

PROCESS FOR THE MANUFACTURE OF ISOBUTYRIC ANHYDRIDE

SUMMARY OF THE INVENTION

The present invention relates to a process for the manufacture of isobutyric anhydride.

It has been known for long that it is possible to prepare a carboxylic acid anhydride by reacting acetic anhydride with a carboxylic acid corresponding to the desired anhydride.

French Patent FR-B-784 458 describes the preparation of propanoic, butyric and caproic anhydrides by reaction between acetic anhydride and propanoic, butyric or caproic acid, respectively, distilling the acetic acid generated as it is formed.

European Patent Application No. EP-A-4 641 describes a continuous or batch process for the preparation of carboxylic anhydrides, such as benzoic, hexahydrobenzoic and trimethylacetic anhydrides, by reaction between the carboxylic acids and acetic anhydride, preferably in stoichiometric proportions.

French Patent FR-B-2 514 345 describes the manufacture of isobutyric anhydride from propylene by carboxylation in liquid hydrogen fluoride, followed by partial hydrolysis of the isobutyryl fluoride. This process is difficult to carry out given the nature of the products used.

The aim of the present invention is therefore to provide a process for the manufacture of isobutyric anhydride which is much simpler in its implementation than the process known according to FR-B-2 514 345 and which makes it possible to obtain an isobutyric anhydride of excellent purity under improved conditions compared with the process according to FR-B-784 458.

The subject of the present invention is a process for the manufacture of isobutyric anhydride by reacting acetic anhydride with isobutyric acid, distilling the acetic acid generated as it is formed, characterized in that the reactor is initially loaded with at least a portion of one of the reagents and a portion of the other such that the reagents are in an excess molar ratio relative to the stoichiometry of one of the reagents, and the reaction is carried out while adding the remainder of the reagents as the reaction progresses and according to the place left free in the reactor by the distillation of the acetic acid produced by the reaction, until the desired overall molar ratio of the reagents is reached.

There is thus used the so-called <<deferred addition>> technique in a batch reaction with shifting of the various equilibria which exist between the species present. Such a technique has made it possible to obtain, surprisingly, a markedly increased production of isobutyric anhydride.

Advantageously, the reaction is performed without addition of catalyst.

In accordance with a particular embodiment of the process according to the present invention, the totality of one of the reagents and a portion of the second are initially loaded.

The overall isobutyric acid/acetic anhydride molar ratio (after addition of the reagent(s) partially loaded initially) may be between 0.5 and 5, in particular between 1.5 and 2.2.

The initial isobutyric acid/acetic anhydride or acetic anhydride/isobutyric acid molar ratio may advantageously be between 0.2 and 1.

The reaction is advantageously performed in a stirred reactor surmounted by a distillation column whose efficiency is preferably at least 8 theoretical plates. Indeed, the column should be sufficiently efficient to avoid bringing the acetic anhydride over with the acetic acid, the purity of the distilled acetic acid being dependent on the column efficiency.

The reactor is advantageously heated by circulation of a heat transfer fluid in a jacket or by recirculation through a heat exchanger.

The column packing may be a structured or a conventional bulk packing or a bulk/structured mixture.

The reaction is generally performed at a temperature of 70 to 150° C., preferably of 100 to 120° C. Temperatures below 70° C. are possible but at the expense of the kinetics of the reaction.

Maintaining the temperature at the desired value is achieved by adjusting the pressure in the reactor.

The reaction is generally performed at a pressure of between $5.33 \times 10^4$ Pa (400 mmHg) and $0.67 \times 10^4$ Pa (50 mmHg).

Advantageously, the desired temperature at the top of the column is adjusted according to the pressure so as to correspond to the temperature for distillation of the acetic acid during the whole reaction.

After completion of the reaction, it is possible to purify the crude material by distilling the excess acetic anhydride and the residual mixed anhydride.

The isobutyric anhydride thus prepared has a purity greater than 98%. A purity of more than 99% can be obtained by distilling the crude material.

EXAMPLES

The following examples illustrate the present invention without however limiting the scope. In these examples, the percentages are percentages by mass.

Example 1

Comparative

Into a mechanically stirred reactor (anchor-type stirrer), heated by circulation of a heat transfer fluid in a jacket, and surmounted by a distillation column with Multiknit® packing, having an efficiency equal to 9 theoretical plates, with a condenser at the top, a vacuum separator, a receiver and a trap, there are introduced all at once:

232.3 g (2.28 mol) of acetic anhydride 320.6 g of isobutyric acid (3.64 mol)

that is in an isobutyric acid/acetic anhydride molar ratio of 1.6.

The initial total load is 552.9 g.

The temperature is kept between 115 and 120° C. during the whole reaction by gradually reducing the pressure from $4.00 \times 10^4$ Pa (300 mmHg) to $1.07 \times 10^4$ Pa (80 mmHg).

The acetic acid produced in the reaction is distilled off as it is formed. A first distillation fraction (F1) of 220 g is thus obtained (purity: 96.1%).

The excess acetic anhydride and the residual mix are removed by distillation at a pressure of $1.07 \times 10^4$ Pa (80 mmHg) (fraction F2: 71 g).

A crude stock (263 g) having a purity of 98.7% is obtained.

If necessary, it is possible to obtain an isobutyric anhydride having a purity greater than 99% by distillation.

Example 2

Of the Invention

The reactor described in Example 1 is loaded with the totality of the acetic anhydride used (411 g) and a portion of the isobutyric acid (141.9 g), that is with an initial isobutyric acid/acetic anhydride molar ratio equal to 0.4.

The initial total load is 552.9 g.

During the reaction phase, as the distillation of the acetic acid progresses, there are continuously added at a rate based on that of the acetic acid distilled, 425.6 g of isobutyric acid such that the final overall isobutyric acid/acetic anhydride molar ratio is equal to 1.6.

The reaction temperature is kept between 115 and 120° C. by gradually reducing the pressure from $5.33 \times 10^4$ Pa (400 mmHg) to $1.60 \times 10^4$ Pa (120 mmHg).

The acetic acid produced in the reaction is removed by distillation as it is formed. A first distillation fraction (F1) of 415 g, having a purity in terms of acetic acid equal to 96%, is thus obtained.

The remainder of the acetic acid, the excess acetic anhydride and the residual mixed anhydride are removed by distillation at $1.07 \times 10^4$ Pa (80 mmHg) (fraction F2: 75 g).

The crude material thus cropped (479 g) has a purity of 98.3%.

A purity of 99% may be obtained by distilling this crude material.

The gain in production for the same initial load of reagents is about 80% without substantial increase in the duration of the reaction.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosure of all applications, patents and publications, cited herein and of corresponding German application No. 103 17 792.2, filed Apr. 16, 2003 is incorporated by reference herein.

The preceding examples can be repeated with similar success by substituting the generically or specifically described reactants and/or operating conditions of this invention for those used in the preceding examples. From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the manufacture of isobutyric anhydride, comprising reacting acetic anhydride with isobutyric acid, and distilling the acetic acid generated as it is formed, wherein the reactor is initially loaded with a portion of one of acetic anhydride or isobutyric acid in an excess molar ratio relative to the stoichiometry of the other reactant, and the reaction is carried out while adding the remainder of the reactant not in excess as the reaction progresses and according to space volume free in the reactor by the distillation of the acetic acid produced by the reaction, until a desired overall molar ratio of the reactants is reached.

2. The process according to claim 1, wherein the totality of one of the reactants and a portion of the second are initially loaded.

3. The process according to claim 1, wherein the overall isobutyric acid/acetic anhydride molar ratio is between 0.5 and 5.

4. The process according to claim 3, wherein the desired molar ratio is an overall isobutyric acid/acetic anhydride molar ratio between 1.5 and 2.2.

5. The process according to claim 1, having an initial isobutyric acid/acetic anhydride or acetic anhydride/isobutyric acid molar ratio between 0.2 and 1.

6. The process according to claim 1, performed in a stirred reactor surmounted by a distillation column whose efficiency is at least 8 theoretical plates.

7. The process according to claim 1, performed at a temperature of 70 to 150° C.

8. The process according to claim 1, performed at a pressure of between $5.33 \times 10^4$ Pa (400 mmHg) and $0.67 \times 10^4$ Pa (50 mmHg).

9. The process according to claim 1, wherein the temperature at the top of the column is adjusted according to pressure so as to correspond to the temperature for distillation of the acetic acid during the whole reaction.

10. The process according to claim 1, further comprising purifying crude isobutyric anhydride by distilling excess acetic anhydride and residual mixed anhydride.

11. The process according to claim 1, performed at a temperature of 100 to 120° C.

* * * * *